United States Patent [19]

Montgomery

[11] Patent Number: 4,863,993

[45] Date of Patent: Sep. 5, 1989

[54] SURFACE PRIMING COMPOSITION FOR PROTEINACEOUS SUBSTRATES; METHOD OF MAKING AND USING SAME

[75] Inventor: Robert E. Montgomery, Los Angeles, Calif.

[73] Assignee: OPI Products, Inc., North Hollywood, Calif.

[21] Appl. No.: 130,603

[22] Filed: Dec. 9, 1987

[51] Int. Cl.$^4$ .................. C08F 20/10; C08K 5/10
[52] U.S. Cl. .................. 524/854; 524/317; 52/318
[58] Field of Search .................. 536/318; 524/317

[56] References Cited

U.S. PATENT DOCUMENTS

| | | | |
|---|---|---|---|
| 4,209,604 | 6/1980 | Werber | 523/176 |
| 4,229,559 | 10/1986 | Cotter et al. | 526/318 |
| 4,420,599 | 12/1983 | Seki et al. | 526/318 |
| 4,431,787 | 2/1984 | Weber | 526/318 |
| 4,521,550 | 6/1985 | Bowen | 523/116 |
| 4,574,130 | 3/1986 | Potter et al. | 526/318 |
| 4,668,735 | 5/1987 | Fukumoto et al. | 526/318 |

FOREIGN PATENT DOCUMENTS

| | | | |
|---|---|---|---|
| 0036294 | 9/1981 | European Pat. Off. | 526/318 |
| 0230330 | 7/1987 | European Pat. Off. | 526/318 |
| 2557536 | 7/1976 | Fed. Rep. of Germany | |
| 0138034 | 10/1979 | Japan | 526/318 |

*Primary Examiner*—Joseph L. Schofer
*Assistant Examiner*—N. Sarofim
*Attorney, Agent, or Firm*—Blakely, Sokoloff, Taylor & Zafman

[57] ABSTRACT

An invented composition for promoting the adhesion of adhesives, coatings and/or composites to proteinsceous substrates is disclosed comprising a water-miscible solvent; and an unsaturated caboxylic acid of the general formula:

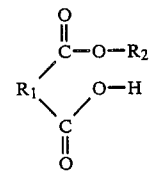

where $R_1$ is selected from $CH=CH$, $C(CH_3)=C(CH_3)$, $C(CH_3)=CH$, $CH_2CH_2$, or $CH_2CH_2CH_2$; and $R_2$ is selected from a terminally mono-, di-, tri-, or multi- unsaturated group. Methods of making the compound and methods of its use are also disclosed.

17 Claims, No Drawings

SURFACE PRIMING COMPOSITION FOR PROTEINACEOUS SUBSTRATES; METHOD OF MAKING AND USING SAME

FIELD OF THE INVENTION

This invention relates to materials and methods for improving the adhesion of adhesives, coatings and composites to biological substrates, particularly proteinaceous surfaces, and more specifically to materials and methods for improving the adhesion of free radical polymerizable adhesives, coatings and composites to proteinaceous substrates in vivo. Even more specifically, materials and methods for increasing the bond strength of adhesives, coatings and composites to proteinaceous substrates for the purpose of restoration and adornment thereof with cosmetic prostheses are herein described.

DESCRIPTION OF THE PRIOR ART

The reparation, adornment, and prosthetic extension of keratinaceous structures, namely, human fingernails and toe nails and livestock hoofs, has been a common practice for centuries. Fingernails are currently known to be coated with multicolored nitrocellulose lacquers, repaired with cyanoacryalate adhesives, and extended with the use of acrylic monomer and polymer slurries or doughs that cure by peroxide/amine free radical mechanisms. Although the nitrocellulose lacquers and the cyanoacrylate adhesives and relatively adherent to a fingernail plate, the acrylic materials employed for the purpose of creating an artificial fingernail prosthesis are not. Only after treatment of the fingernail surface with an unsaturated carboxylic acid, such as methacrylic acid (current commercial embodiments containing in excess of 70 percent methacrylic acid), will such acrylic monomer and polymer slurries or doughs adhere to the nail plate. Such harsh treatment on a relatively fragile surface poses a serious toxicological hazard due to the corrosive nature of the unsaturated carboxylic acids. Other unsaturated carboxylic acids presently being used in the described applications include either alone or in part, acrylic acid and beta-carboxyethyl acrylate. Lower concentrations of these unsaturated acids pose a decreased danger to the intact fingernail surface; however, at such lower concentration the adhesion of the acrylic monomer and polymer slurry is minimized or lost completely. An analogous situation exists when attempting to repair a split or fractured hoof in that without the application of the corrosive and possibly toxic levels of unsaturated acids, very poor adhesion results.

Currently, the only known and readily practiced method for obtaining adhesion of prosthetic materials to wholly proteinaceous substrates, such as fingernails and hooves, has been the physical abrasion and roughening of the proteinaceous substrate surface with a file, sandpaper-like, or other abrasive material, followed by the application of unsaturated carboxylic acid solutions (known in the artificial fingernail art as primers), followed lastly by the application of the prosthetic material. The prosthetic material is not inherently adhesive to proteinaceous substrates. Rather, the prosthetic material also contains unsaturated groups, which, when curing, chemically react with the unsaturated groups of the carboxylic acid solution applied to the proteinaceous substrate. Thus, an adhesive bond between said substrate and the prosthesis is provided.

The disadvantages of such a method and materials used in the prior art are as follows:

(1) too much physical abrasion or roughening of the proteinaceous substrate, particularly a living fingernail, can be harmful to the substrate;

(2) in the area of hoof binding, cracks and fissures in the hooves are not readily abraded or roughened due to the inaccessibility of the surface to such abrasive materials and methods;

(3) the unsaturated carboxylic acids that are often used (acrylic acid and methacrylic acid, either alone at full concentration of in combination with other diluents, are highly corrosive and can severely damage the protein of a fingernail or hoof or the underlying or surrounding living tissue; and (4) even with such harsh surface preparation as described above, the adhesive bonds obtained with such methods are poor and all too often inadequate to retain the prosthetsis for sufficient periods of time or under stress, thus causing the prosthetsis to break off in whole or in part.

A number of patents showing various prior art adhesive compositions and fingernail treatments have been noted, including U.S. Pat. Nos. 4,547,363, 4,209,604, 4,413,108, 4,521,550 and German Pat. No. DT 2557536.

U.S. Pat. No. 4,547,363 discloses a fingernail strengthener deposited from solution onto the fingernail surface. These compositions are of no utility in achieving high bond strengths between proteinaceous substrates (such as fingernails) and free-radically polymerized adhesives, coatings or composites.

U.S. Pat. No. 4,521,550 discloses materials and methods for obtaining high bond strengths to dentin, which is a partially proteinaceous substrate. The adhesion promoters of that invention are limited to the addition reaction product of pyromellitic acid dianhydride and 2-hydroxyethyl methacrylate (PMDM), the addition reaction product of 3,3′,4,4′-benzophenonetetracarboxylic dianhydride and 2-hydroxyethyl methacrylate (BTDA-HEMA) and 4-methacryloxyethyltrimellitic anhydride (4-META). PMDM is shown herein to be inferior to the compositions of the present invention for achieving high bond strength to proteinaceous substrates.

The remaining patents noted above disclose a number of unsaturated carboxylic acid compounds to be included in anaerobic adhesive compositions. These compositions are solvent-free. Most important, however, is that they are of no utility in covering, protecting or adorning surfaces, such as fingernails and livestock hooves, which are exposed to air (aerobic surfaces).

SUMMARY OF THE INVENTION

The present invention comprises materials and methods which substantially increase the adhesive bond strength between adhesives, coatings or composites, and proteinaceous biological substrates such as fingernails and livestock hooves. The purpose of this invention is to provide materials and methods for improved adhesive bonding of both composite and unfilled coating and adhesive resins capable of free radical-type polymerization to biological substrates composed wholly or in part of protein.

Briefly, the method of this invention is preferably accomplished by treating the substrate to be adhered to with a non-aqueous solution of an addition reaction product between a cyclic anhydride and a terminally unsaturated molecule containing at least one hydroxyl group. An example of such a compound is the addition reaction product of maleic anhydride and 2-hydroxyethyl methacrylate. The solution carrier is preferably a nonaqueous solvent capable of (1) dissolving the said addition reaction product(s) described above without precipitation or polymerization during storage and (2) forming a mixture, preferably azeotropic, with water.

A most preferred embodiment of the invention utilizes the addition reaction product of maleic anhydride and 2-hydroxyethyl methacrylate in a carrier solvent of ethyl acetate. This solution is brushed, sprayed or otherwise applied to the substrate to be bonded and the ethyl acetate is allowed to completely evaporate. An adhesive, coating or composite is then applied to the treated substrate and subsequently polymerized by a free radical mechanism. The polymerized adhesive, coating or composite will be seen to adhere tenaciously to the pretreated substrate, achieving bond strengths unexpectedly high compared to pretreatment with other carboxyl-containing unsaturated adhesion promoters such as methacrylic acid ($CH_2=C(CH_3)COOH$). The adhesion promoting addition reaction products of the present invention can be described in general as:

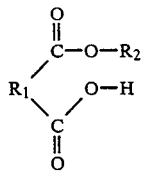

where $R_1$ is selected from $CH=CH$, $C(CH_3)=C(CH_3)$, $C(CH_3)=CH$, $CH_2CH_2$, and $CH_2CH_2CH_2$; and $R_2$ is selected from a terminally mono-, di-, tri-, or multifunctional unsaturated group.

As mentioned previously, these compounds are addition reaction products between a cyclic anhydride and a hydroxyl-containing terminally unsaturated molecule. Examples of cyclic anhydride precursors suitable for obtaining these addition reaction products are maleic anhydride, dimethylmaleic anhydride, succinic anhydride, glutaric anhydride, and citraconic anydride. Any cyclic anhydride capable of ring opening during the addition reaction is contemplated. Examples of hydroxyl-containing terminally unsaturated molecules suitable for achieving the addition reaction products of this invention are 2-hydroxyethyl (meth)acrylate, 2-hydroxypropyl (meth)acrylate, 2-hydroxybutyl (meth)acrylate, allyl alcohol, pentaerythritol tri(meth)acrylate, N-2-hydroxyethyl (meth)acrylamide and methallyl alcohol. Any compound containing at least one hydroxyl group and at least one terminal unsaturated group (acrylate, methacrylate, vinyl, acrylamide, methacrylamide, etc.) is contemplated to have utility in the manufacture of the addition reaction products of the present invention.

Examples of the addition reaction products of this invention are (meth)acryloyloxyethyl maleate, (meth)acryloyloxypropyl maleate, (meth)acryloyloxybutyl maleate, (meth)acryloyloxyethyl citraconate, (meth)acryloyloxypropyl citraconate, (meth)acryloyloxybutyl citraconate, (meth)acryloyloxyethyl dimethylmaleate, (meth)acryloyloxypropyl dimethylmaleate, (meth)acryloyloxybutyl dimethylmaleate, (meth)acryloyloxyethyl succinate, (meth)acryloyloxyethyl glutarate, (meth)allyloyloxyethyl maleate and others.

A variety of solvents and solvent mixtures are useful for the practice of this invention. These solvents are desirably volatile and water-miscible, as well as being good solvents for the adhesion promoters described above. More desirably they are capable of forming azeotropic mixtures with water, specifically for displacing adsorbed moisture at the adhesion promoter/substrate interface. This adsorbed moisture is undesirable when attempting to achieve high blood strengths and decreases adhesion of adhesives, coatings and composites to a variety of substrates. An example of this decreased adhesion is observed on glass, which has a tendency to adsorb a layer of water, especially under high humidity conditions. Thus displacement of adsorbed moisture is advantageous in achieving a high degree of adhesion. Suitable solvents include, but are not limited to, acetone, ethyl acetate, isopropyl alcohol, ethanol, butyl acetate, n-propyl acetate, isopropyl acetate, cyclohexane, n-hexane, isobutyl acetate, sec-butyl acetate, amyl acetate, isoamyl acetate, butanol, acetonitrile, N-methyl pyrollidone, tetrahydrofuran, butyrolactone, and mixtures thereof. In formulating the adhesion promoting solutions of this invention that are intended for contact in vivo, attention should be paid to the use of solvents that are not harmful or dangerous to living tissue or pose a significant environmental or work place hazard. The most preferred solvents are ethyl acetate, isopropanol, ethanol and mixtures thereof. All three of these solvents are capable of forming azeotropic mixtures with water, are relatively innocuous with respect to their interaction with living tissue, dissolve the adhesion promoting agents of this invention, and are sufficiently volatile to evaporate completely in a reasonable amount of time.

After priming the surface of a proteinaceous substrate with a composition of the type disclosed herein, the surface may then be contacted with an adhesive, coating or composite providing greater adherence of such materials to the primed substrate, than to an unprimed substrate.

DESCRIPTION OF PREFERRED EMBODIMENTS

In general, this invention comprises materials and methods for improving the adhesive strength of adhesives, coatings and composites to biological substrates. The terms "adhesives, coatings and composites" are taken to mean any composition that can be stored in either a single or multi-component form, is used to adhere, cover, adorn, replace, or otherwise protect a surface, and can be polymerized by one or more of a variety of free radical-type initiation processes. Examples of such materials are (1) two-component (powder and liquid) artificial fingernail prosthesis formulations, which polymerize through a peroxide/tertiary amine type initiation;

(2) one component, glass/resin dental compositions, which are polymerized by actinic (visible and/or ultraviolet) light activation of a photoinitiator, together with an optional tertiary amine; and (3) ultraviolet and visible light cured, unfilled or filled, coatings and adhesives used to attach and/or cover natural or artificial fingernails; similar compositions are utilized for the reparation of livestock hooves that have become split or cracked.

Although not limited to the above types of adhesives, coatings and composites, the three categories listed are those compositions that show marked improvement in adhesive strength through the practice of the present invention.

The most preferred inventive method for pretreating the surfaces to be adhered to comprises contacting the surface with a non-aqueous solution of a methacryloyloxyethyl maleate (herein referred to as MAHEMA), and allowing the non-aqueous solvent to completely evaporate. Then, the adhesive, coating or composite is allowed to contact the treated surface and polymerized through free radical mechanisms. The preferred concentration of MAHEMA in the non-aqueous solvent is from about one percent to about 30 percent, and the most preferred concentration is about 5 to 20 percent. Differences in the porosity and surface free energy of the substrate will have a bearing on the optimal MAHEMA concentration for each individual surface to be "primed". In general, following the complete evaporation of the carrier solvent, the treated substrate should appear relatively dry. Treated surfaces that appear shiny and wet tend to have a thick layer of residual MAHEMA, which can act as a boundary layer and lead to decreased adhesive strength.

SYNTHESIS OF MAHEMA

MAHEMA was prepared by heating together 1 mole of maleic anhydride and in slight excess of 1 mole of 2-hydroxyethyl methacrylate together with about 200 ppm of the monomethyl ether of hydroquinone as a stabilizer against premature polymerization. In addition 500 ppm of triethylamine was included in the reaction mixture as a catalyst for the addition reaction. Upon cooling, a slightly yellow, moderately viscous liquid is obtained, having a refractive index of 1.484 (at 20 degrees C.) and a Brookfield viscosity (at 23 degrees C.) of 470. cps. This liquid was stored in amber glass bottles until further use. The structure of MAHEMA is as follows:

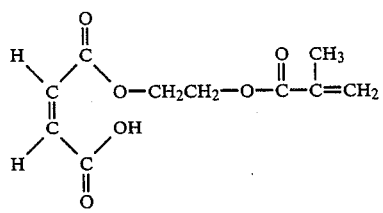

Care must be taken during the heating process above to keep the reaction process at or below about 80–90 degrees C. to avoid premature polymerization due to the methacrylate group.

Alternatively, MAHEMA may be synthesized in the solvent carrier to be used in the practice of this invention. For example, the properly calculated amounts of maleic anhydride and 2-hydroxyethyl methacrylate may be added to ethyl acetate to provide the desired final concentration of MAHEMA in situ. Attention must be paid to this method of synthesizing MAHEMA, in that certain solvents, such as isopropyl alcohol, can compete with the 2-hydroxyethyl methacrylate for addition to the anhydride group of maleic anhydride.

ADHESIVE STRENGTH OF ADHESIVES, COATINGS AND COMPOSITES ON PROTEINACEOUS SUBSTRATES

Proteinaceous substrates were tested to demonstrate the adhesive strength improvement caused by the adhesion promoting compositions of this invention. The differences in the adhesive strength provided by pretreating the substrate with the present invention relative to prior art systems are shown.

EXAMPLE 1

Solutions ranging from one to 30 percent MAHEMA in anhydrous ethyl acetate were prepared and packaged in amber glass bottles with a polyethylene brush cap for application to the surfaces to be tested. In order to test the extent of adhesion improvement by the MAHEMA solutions on keratinaceous substrates, cattle hooves were chosen due to their availability and ease of handling during tensile adhesive strength testing. Flat sections of cattle hooves were prepared with the hoof fibers running parallel to the surface to be tested. The hoof surface was then abraded with a fine grit sandpaper and subsequently rinsed with water and allowed to dry thoroughly. The abraded and rinsed hoof surface was then treated with the MAHEMA solution, being brushed on and allowing the ethyl acetate to evaporate completely. The surface of the hoof at this point appeared dry and slightly glossy. A stainless steel cylinder with a tapered bore and an access port was then contacted to the treated hoof surface perpendicularly.

The following formulation was mixed, poured into the testing cylinder through the access port, and allowed to polymerize. This assembly was allowed to age at room temperature for 24 hours and subsequently tested for tensile adhesive strength in an Instron Tensile Strength Tester Model 1011 (Instron Corp, Quincy, MA) at a crosshead speed of 0.1 mm/minute.

Liquid A

| Ethyl methacrylate | 93% |
| Ethylene glycol dimethacrylate | 6% |
| Dimethyl-p-toluidine | 1% |

Powder B

| Poly(ethyl-co-methyl methacrylate) polymer | 98.1% |
| Benzoyl peroxide | 1.9% |

Ratio of Liquid A:Powder B is approximately 1:3 in the final mixture.

The following results were obtained.

| MAHEMA % | Avg. Adh.* | Adh. Range** | No. Measurements |
| --- | --- | --- | --- |
| 0 | 240 | 110–330 | 5 |
| 1 | 570 | 400–670 | 5 |
| 2 | 720 | 460–790 | 5 |
| 3 | 780 | 600–840 | 5 |
| 4 | 800 | 690–880 | 5 |
| 5 | 870 | 810–910 | 5 |
| 8 | 080 | 940–1170 | 5 |
| 10 | 1410 | 1250–1500 | 5 |
| 13 | 1840 | 1610–1990 | 5 |
| 16 | 2320 | 1980–2500 | 5 |
| 20 | 2450 | 2020–2610 | 5 |

-continued

| MAHEMA % | Avg. Adh.* | Adh. Range** | No. Measurements |
|---|---|---|---|
| 25 | 2030 | 1880–2150 | 5 |
| 30 | 1490 | 1200–1780 | 5 |

*Average adhesion in psi (lbs per sq. inch)
**Adhesion range in psi (lbs per sq. inch)

EXAMPLE 2

The adhesion promoting capabilities of the maleic anhydride addition reaction products of this invention were compared to those of other known and/or potential adhesion promoters. All compounds tested had at least one carboxylic group and at least one unsaturated group capable of participating in free radical type polymerizations. Each promoter is listed below, together with it's concentration, solvent (if any), substrate appearance, and tensile adhesive strength as described in Example 1.

| Adhesion Promoter | Conc. | Solvent | Avg. Adh[3] |
|---|---|---|---|
| Methacrylic acid | 20% | Ethyl acetate | 680 |
| Methacrylic acid | 100% | None | 1250 |
| Acrylic acid | 20% | Ethyl acetate | 820 |
| Acrylic acid | 100% | None | 1500 |
| MAHEMA[4] | 20% | Ethyl acetate | 2510 |
| PMDM[1] | 5% | Acetone | 1110 |
| PMDM[1] | 20% | Acetone | 730 |
| Maleic acid | 20% | Ethyl acetate | 300 |
| MAHPMA[2,4] | 20% | Ethyl acetate | 2480 |

[1]Pyromellitic dianhydride/2-hydroxyethyl methacrylate adduct (ref. Patent No. 4,521,550)
[2]Maleic anhydride/2-hydroxypropyl methacrylate adduct
[3]average adhesion in psi (lbs per sq. inch)
[4]Invented Compositions It is anticipated that just about any substrate comprised entirely or in part of protein will be adhered to better by pretreatment of the substrate surface with the compositions of this invention. The preceding disclosure has demonstrated the improved adhesion of a free-radical initiated composition to keratin substrates treated with MAHEMA and other cyclic anhydride addition reaction products as previously described. It is believed that substrates such as fingernails, hooves, bone, ivory, leather, dentin, enamel, and other partially or wholly proteinaceous materials will show the adhesion-promoted benefits of the present inventive compositions.

What I claim is:

1. A pretreatment composition for increasing the adhesion of adhesives, coatings and/or composites to proteinaceous substrates comprising:
    (a) a water-miscible solvent; and
    (b) an unsaturated carboxylic acid of the general formula:

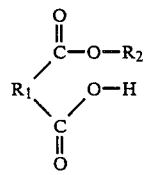

where $R_1$ is selected from $CH=CH$, $C(CH_3)=C(CH_3)$, $C(CH_3)=CH$, $CH_2CH_2$, or $CH_2CH_2CH_2$; and $R_2$ is selected from a terminally mono-, di-, tri-, or multi-unsaturated group.

2. The composition set forth in claim 1 wherein said unsaturated carboxylic acid is selected from (meth)acryloyloxyethyl maleate, (meth)acryloyloxypropyl maleate, (meth)acryloyloxybutyl maleate, (meth)acryloyloxyethyl citraconate, (meth)acryloyloxypropyl citraconate, (meth)acryloyloxybutyl citraconate, (meth)acryloyloxyethyl dimethylmaleate, (meth)acryloyloxypropyl dimethylmaleate, (meth)acryloyloxybutyl dimethylmaleate, (meth)acryloylethyl succinate, (meth)acryloyloxyethyl glutarate and (meth)allyloyloxyethyl maleate.

3. The composition set forth in claim 2 wherein said unsaturated carboxylic acid is methacryloyloxyethyl maleate.

4. The composition set forth in claim 1 wherein said water-miscible solvent is selected from partially and wholly water-miscible solvents.

5. The composition set forth in claim 1 wherein said water-miscible solvent is selected from acetone, ethyl acetate, isopropyl alcohol, ethanol, butyl acetate, n-propyl acetate, isopropyl acetate, cyclohexane, n-hexane, isobutyl acetate, sec-butyl acetate, amyl acetate, isoamyl acetate, butanol, acetonitrile, N-methyl pyrollidone, tetrahydrofuran, butyrolactone, and mixtures thereof.

6. The composition as set forth in claim 5 where the water-miscible solvent is ethyl acetate.

7. The composition of claim 6 wherein said unsaturated carboxylic acid is selected from (meth)acryloyloxyethyl maleate, (meth)acryloyloxypropyl maleate, (meth)acryloyloxybutyl maleate, (meth)acryloyloxyethyl citraconate, (meth)acryloyloxypropyl citraconate, (meth)acryloyloxybutyl citraconate, (meth)acryloyloxyethyl dimethylmaleate, (meth)acryloyloxypropyl dimethylmaleate, (meth)acryloyloxybutyl dimethylmaleate, (meth)acryloyloxyethyl succinate, (meth)acryloyloxyethyl glutarate and (meth)allyloyloxyethyl maleate.

8. The composition of claim 8 wherein said composition comprises 1 to 30% by weight methacryloyloxyethyl maleate.

9. The composition of claim 8 comprising 5–20% by weight methacryloyloxyethyl maleate.

10. The composition of claim 9 comprising 10% by weightmethacryloyloxyethyl maleate.

11. A pretreatment composition for increasing the adhesion of adhesives, coatings and/or composites to proteinaceous substrates comprising:
    (a) a water-miscible solvent; and
    (b) an unsaturated carboxylic acid of the formula:

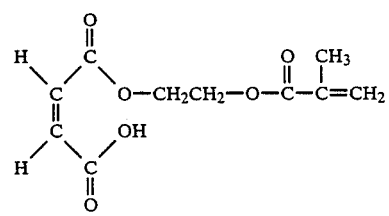

12. The composition set forth in claim 11 wherein said water-miscible solvent is selected from acetone, ethyl acetate, isopropyl alcohol, ethanol, butyl acetate, n-propyl acetate, isopropyl acetate, cyclohexane, n-hexane, isobutyl acetate, sec-butyl acetate, amyl acetate, isoamyl acetate, butanol, acetonitrile, N-methyl pyrollidone, tetrahydrofuran, butyrolactone, and mixtures thereof.

13. The composition as set forth in claim 8 wherein the water-miscible solvent is ethyl acetate.

14. The composition as set forth in claim 13 wherein said composition comprises 1 to 30% by weight methacryloyloxyethyl maleate.

15. The composition as set forth in claim 14 wherein said composition comprises 5 to 20% by weight methacryloyloxyethyl maleate.

16. The composition as set forth in claim 15 wherein said composition comprises 10% by weight methacryloyloxyethyl maleate.

17. A pretreatment composition for increasing the adhesion of adhesives, coatings and/or composites to proteinaceous substrates comprising:
   (a) ethyl acetate; and
   (b) 10% by weight methacryloyloxyethyl maleate.

* * * * *

UNITED STATES PATENT AND TRADEMARK OFFICE
CERTIFICATE OF CORRECTION

PATENT NO. : 4,863,993
DATED : September 5, 1989
INVENTOR(S) : Montgomery, Robert E.

It is certified that error appears in the above-identified patent and that said Letters Patent is hereby corrected as shown below:

On the title page assignee should read

--(73) Assignee: REM Systems, Inc.--.

Column 4, line 11, delete "blood" insert --bond--.

Column 8, line 41, delete "claim 8" insert -- claim 1 --.

Signed and Sealed this

Twenty-third Day of October, 1990

Attest:

HARRY F. MANBECK, JR.

*Attesting Officer*  *Commissioner of Patents and Trademarks*

UNITED STATES PATENT AND TRADEMARK OFFICE
CERTIFICATE OF CORRECTION

PATENT NO. : 4,863,993

DATED : 9/5/89

INVENTOR(S) : Montgomery

It is certified that error in the above-identified patent and that said Letters Patent is hereby corrected as shown below:

col. 01, line 31     delete "and"     insert --are--

Signed and Sealed this

Sixteenth Day of July, 1991

*Attest:*

HARRY F. MANBECK, JR.

*Attesting Officer*     *Commissioner of Patents and Trademarks*